United States Patent
Rozynes et al.

(10) Patent No.: US 10,492,944 B2
(45) Date of Patent: Dec. 3, 2019

(54) EYE AILMENT TREATMENT APPARATUS

(71) Applicants: Linda Rozynes, Miami, FL (US); Noah McNeely, Lawrenceville, GA (US)

(72) Inventors: Linda Rozynes, Miami, FL (US); Noah McNeely, Lawrenceville, GA (US)

(*) Notice: Subject to any disclaimer, the term of this patent is extended or adjusted under 35 U.S.C. 154(b) by 0 days.

(21) Appl. No.: 16/396,933

(22) Filed: Apr. 29, 2019

(65) Prior Publication Data

US 2019/0336329 A1    Nov. 7, 2019

Related U.S. Application Data

(63) Continuation-in-part of application No. 15/970,019, filed on May 3, 2018.

(51) Int. Cl.
*A61F 7/02* (2006.01)
*A61F 7/00* (2006.01)
*A61F 7/03* (2006.01)

(52) U.S. Cl.
CPC .......... *A61F 7/02* (2013.01); *A61F 7/03* (2013.01); *A61F 2007/0004* (2013.01); *A61F 2007/0087* (2013.01); *A61F 2007/0088* (2013.01); *A61F 2007/0203* (2013.01); *A61F 2007/0282* (2013.01)

(58) Field of Classification Search
CPC ...... A61F 2007/0004; A61F 2007/0054; A61F 2007/0087; A61F 2007/0088; A61F 2007/0203; A61F 2007/0204; A61F 2007/0211; A61F 2007/0219; A61F 2007/022; A61F 2007/026; A61F 2007/0268; A61F 7/02; A61F 7/03; A61F 9/0026

See application file for complete search history.

(56) References Cited

U.S. PATENT DOCUMENTS

| | | | | |
|---|---|---|---|---|
| 6,116,426 A * | 9/2000 | Slonim | ................ | A61F 17/00 206/499 |
| 7,513,893 B2 * | 4/2009 | Soroudi | ................ | A61F 7/03 604/289 |
| 8,235,954 B2 * | 8/2012 | Soroudi | ................ | A61F 7/03 604/289 |
| 2005/0119629 A1 * | 6/2005 | Soroudi | ................ | A61F 9/0017 604/289 |
| 2006/0018953 A1 * | 1/2006 | Guillon | ................ | A61F 7/034 424/443 |

(Continued)

*Primary Examiner* — Kaitlyn E Smith
*Assistant Examiner* — Bradford C. Blaise
(74) *Attorney, Agent, or Firm* — Dale J. Ream (57) ABSTRACT

An eye ailment treatment apparatus includes a case having an outer wall that has a front end and a rear end opposite the front end, the outer wall defining an interior area and having an outlet port at the front end. A water reservoir is positioned in the interior area and in operable communication with the outlet port. A pump is operably coupled to the water reservoir for pumping water from the water reservoir to the outlet port when actuated. An actuator is positioned on the outer wall and operably coupled to the pump for actuating the pump when operated. A treatment head is in fluid communication with the outlet port, the treatment head having an external surface constructed of a soft material for contact with a user's eye and having an unvented internal chamber that includes a exothermal material that generates heat when mixed with water.

8 Claims, 9 Drawing Sheets

(56) References Cited

U.S. PATENT DOCUMENTS

| | | | | |
|---|---|---|---|---|
| 2006/0104914 | A1* | 5/2006 | Soroudi | A61F 7/03 424/45 |
| 2009/0264971 | A1* | 10/2009 | Wickstead | A61F 7/03 607/108 |
| 2010/0125255 | A1* | 5/2010 | Paulson | A61F 7/02 604/291 |
| 2014/0081361 | A1* | 3/2014 | Dhayan | A61F 7/10 607/109 |
| 2015/0182415 | A1* | 7/2015 | Olkowski | A61H 23/02 601/93 |
| 2015/0297394 | A1* | 10/2015 | Young | A61F 7/0097 607/96 |
| 2016/0030233 | A1* | 2/2016 | Millar | A61F 7/007 607/109 |
| 2016/0272925 | A1* | 9/2016 | Lin | C11D 17/049 |
| 2017/0246031 | A1* | 8/2017 | Benyaminpour | B60R 21/235 |
| 2017/0290628 | A1* | 10/2017 | Pepe | A61B 18/1485 |
| 2018/0200106 | A1* | 7/2018 | Zoumalan | A61F 9/0008 |

* cited by examiner

EYE AILMENT TREATMENT APPARATUS

REFERENCE TO RELATED APPLICATIONS

This application claims the benefit of and is a continuation-in-part of patent application Ser. No. 15/970,019 filed May 3, 2018 titled Eye Ailment Treatment Apparatus, which is incorporated in its entirety herein by reference.

BACKGROUND OF THE INVENTION

This invention relates generally to eyelid treatment devices and methods and, more particularly, to a treatment apparatus for treating eye ailments that require heat treatments and relief that includes forcing water into a treatment head that creates an exothermic event that prepares a heated compress for immediate application to an eye stye and other related conditions.

An eye stye is an ophthalmological condition characterized as a small, painful lump on the eyelid or area around an eye. Similar eye irritations include Blepharitis, Chalazia, Conjunctivitis (pink eye), and eye pain in general, and. The lump may be red, filled with pus, and may become painful and infected. Although rarely affecting vision or causing damage to the eye itself, an eye stye usually increases in size and lasts for several days before bursting and then healing.

Various methods have been proposed for treating an eye stye with the goal of decreasing its longevity and minimizing the pain and unsightliness of the event. For instance, most eye or eyelid conditions are improved with contact by a hot compress. Persons with eye irritations have used warm tea-bags, heated potatoes, and even heated spoons. The treatment of an eye stye may need to be repeated multiple times over several days to be effective. Unfortunately, simply warming up and applying a wet washcloth to one's eyelid is difficult, inconvenient, and perhaps not as effective compared to receiving treatment by a medical professional who may have an instrument or warm compress materials that apply to an eye stye more accurately and with greater safety and efficacy.

Therefore, it would be desirable to have an eye stye treatment device having a handle and a treatment portion that a patient user can operate at home or away, as it is portable, to apply a heated treatment head to an eyelid. Further, it would be desirable to have an eye stye treatment device that selectively injects water into a treatment head having a granular material that generates an exothermic event inside an unvented internal chamber that heats a soft padded head which may be touched to the eyelid for treating a stye. In addition, it would be desirable to have an eye stye treatment device that is refillable with water to be injected and in which the treatment head may be replaced with a replacement head easily and after each use.

SUMMARY OF THE INVENTION

An eye ailment treatment apparatus according to the present invention includes a case having an outer wall that has a front end and a rear end opposite the front end, the outer wall defining an interior area and having an outlet port at the front end. A water reservoir is positioned in the interior area and in operable communication with the outlet port. A pump is operably coupled to the water reservoir for pumping water from the water reservoir to the outlet port when actuated. An actuator is positioned on the outer wall and operably coupled to the pump for actuating the pump when operated. A treatment head is in fluid communication with the outlet port, the treatment head having an external surface constructed of a soft material for contact with a user's eye and having an unvented and sealed internal chamber that includes an exothermal material that generates heat when mixed with water. The apparatus may include a plurality of replacement treatment heads, each replacement head being removably coupled to the outlet port when the treatment head coupled to the outlet port is removed, each replacement head having an external surface constructed of a soft material for contact with a user's eye and having an internal chamber that includes a exothermal material that generates heat when mixed with water.

Therefore a general object of this invention is to provide a portable eye ailment treatment apparatus that provides a handheld device useful for home and away from home by a person who has a stye or other eye conditions that require heat in or around her eye.

Another object of this invention is to provide an eye ailment treatment apparatus, as aforesaid, having a handle that includes a water reservoir and a pump for injecting water from the reservoir into a padded treatment head. It will be appreciated that the pump may be a button-actuated pump, a slider-type pump, a squeeze/press, or the like.

Still another object of this invention is to provide an eye ailment treatment apparatus, as aforesaid, having a single use padded treatment head for receiving water into an unvented and sealed internal chamber containing calcium chloride for causing an exothermic reaction that provides heat to the padded head and from which the heated water is not released.

Yet another object of this invention is to provide an eye ailment treatment apparatus, as aforesaid, that is safe to apply heated treatment directly to the stye in the eye region of a person's face.

A further object of this invention is to provide an eye ailment treatment apparatus, as aforesaid, having a storage housing for holding a plurality of replacement treatment heads.

A still further object of this invention is to provide an eye ailment treatment apparatus, as aforesaid, that includes manual activation of a pump for injecting water into the treatment head without need of a battery or other electrical power source.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 5b is an exploded view of the replacement treatment head housing as in FIG. 5a;

FIG. 6a is an end view of the replacement treatment head housing as in FIG. 5a;

FIG. 6b is a sectional view taken along line 6b-6b of FIG. 6a;

DESCRIPTION OF THE PREFERRED EMBODIMENT

An eye ailment treatment apparatus according to a preferred embodiment of the present invention will now be described in detail with reference to FIGS. 1 to 8 of the accompanying drawings. The eye ailment treatment apparatus 10 includes a case 20, a water reservoir 30 positioned in the case 20, and a treatment head 40 removably coupled to the case 20 in fluid communication with the reservoir 30.

The case 20 includes an outer wall having a front end 22 and a rear end 24 opposite the front end 22. The outer wall may have a generally cylindrical configuration and be referred to as a continuous outer wall although the outer wall may have an ergonomic and, thus, irregular shape or may even be rectangular having multiple connected side walls. The outer wall of the case 20 defines an interior area for containing other components as will be described below. The case 20 includes an outlet port 26 at the front end 22 to which the treatment head 40 may be coupled as described later.

The case 20 serves as a handle to be held by a user when applying the treatment head 40 to the stye in the eye region of his head. Accordingly, the case 20 is preferably easy and stable to grip. Specifically, the outer wall may include an elastomeric or rubber overmold 28 that covers all or part of the surface thereof. Overmolding is a process where a single part is created using two or more different materials in combination. Typically the first material, sometimes referred to as the substrate, is partially or fully covered by subsequent materials (overmold materials) during the manufacturing process. In the present instance, the rubber layer is overlaid atop the otherwise plastic material of the outer wall. It will be appreciated that the overmold technique may be applied to any of the handle surfaces and any two layers thereof.

Figure 2A:
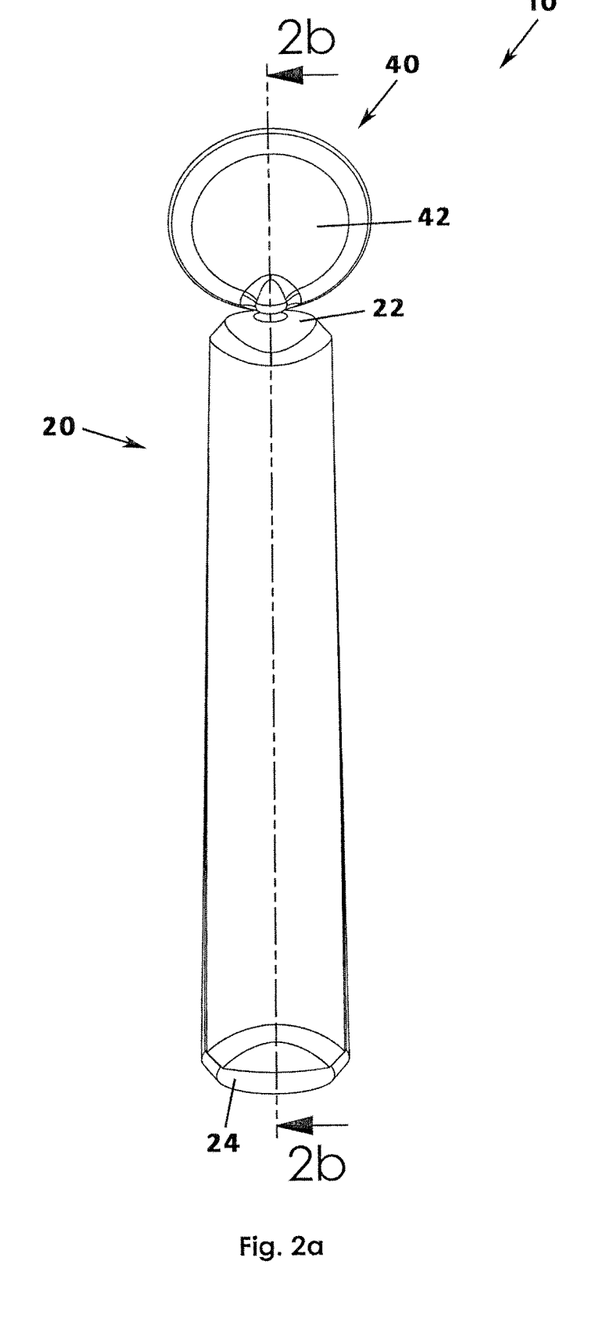
FIG. 2a is a side view of the eye ailment treatment apparatus as in FIG. 1.
Figure 2B:
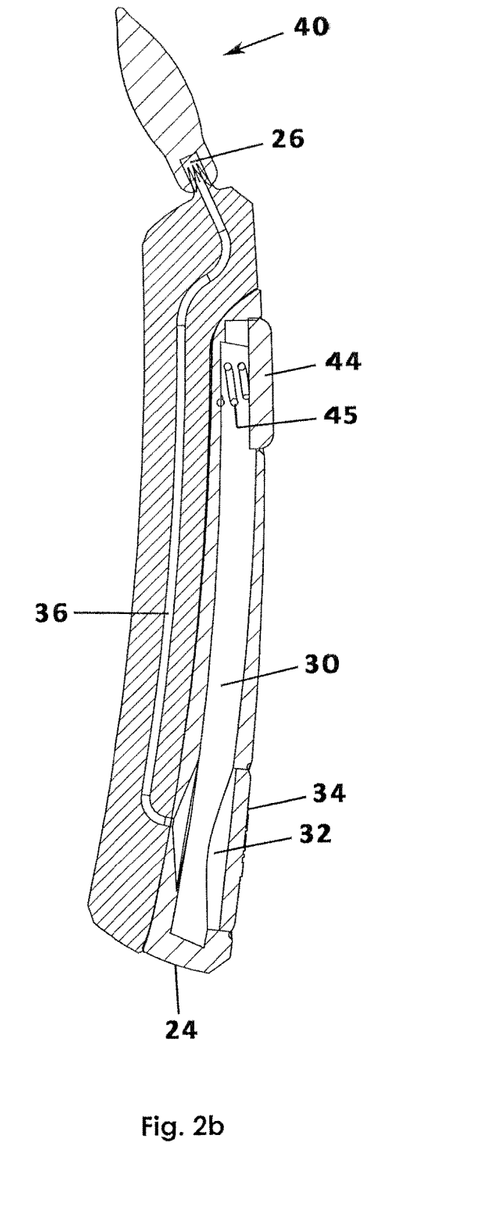
FIG. 2b is a sectional view taken along line 2b-2b of FIG. 2a illustrating the actuator in a normal released configuration.
Figure 2C:
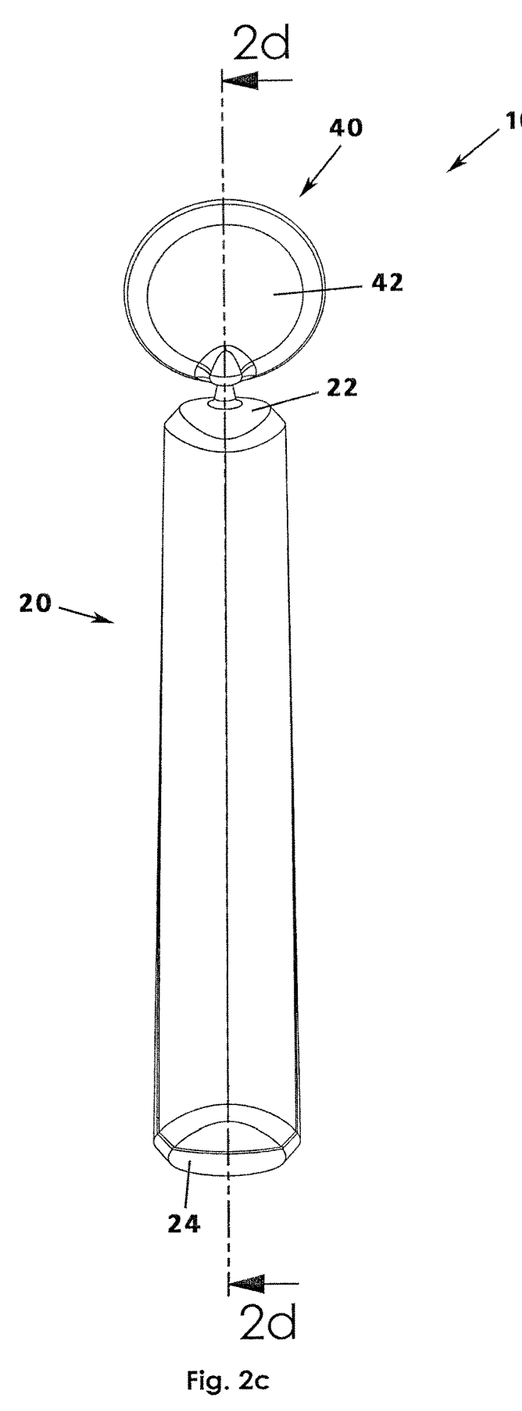
FIG. 2c is a side view of the eye ailment treatment apparatus as in FIG. 1.

The water reservoir 30 is positioned within the interior area of the case 20 and may include a plastic housing or flexible bag construction. In either case, the water reservoir 30 is operable to hold a predetermined quantity of water. The outer wall includes a refill port 32 in fluid communication with the water reservoir 30 and may include a refill door 34 (or other cover such as a flap threaded cover or the like) pivotally movable between an open configuration allowing access to the water reservoir 30 and a closed configuration not allowing access thereto. In other words, the refill door 34 may be opened to insert more water and closed during use and to prevent spillage (FIG. 2b).

Figure 1:
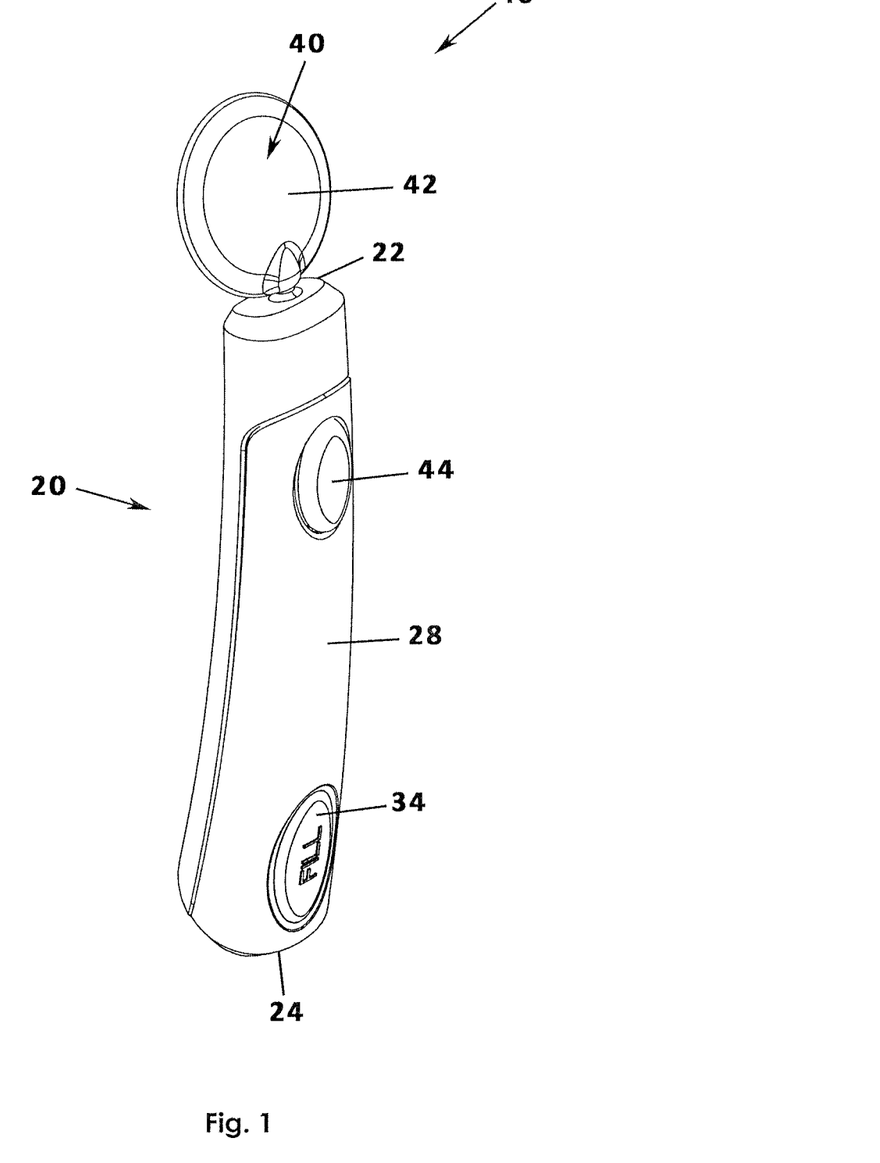
FIG. 1 is a perspective view of an eye ailment treatment apparatus according to a preferred embodiment of the present invention.
Figure 2D:
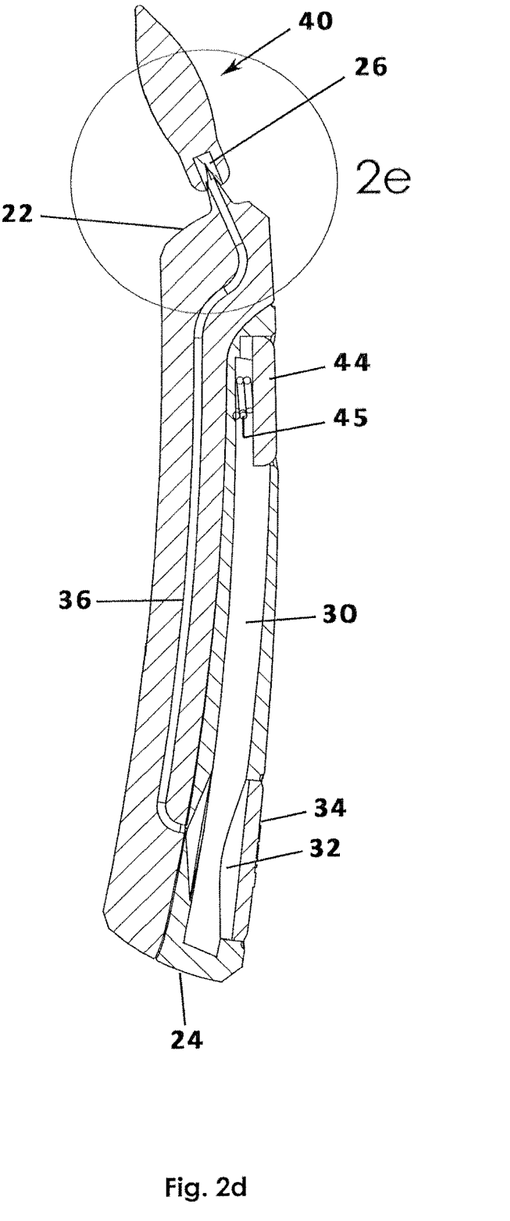
FIG. 2d is a sectional view taken along line 2d-2d of FIG. 2c illustrating the actuator in a normal actuated configuration.
Figure 2E:
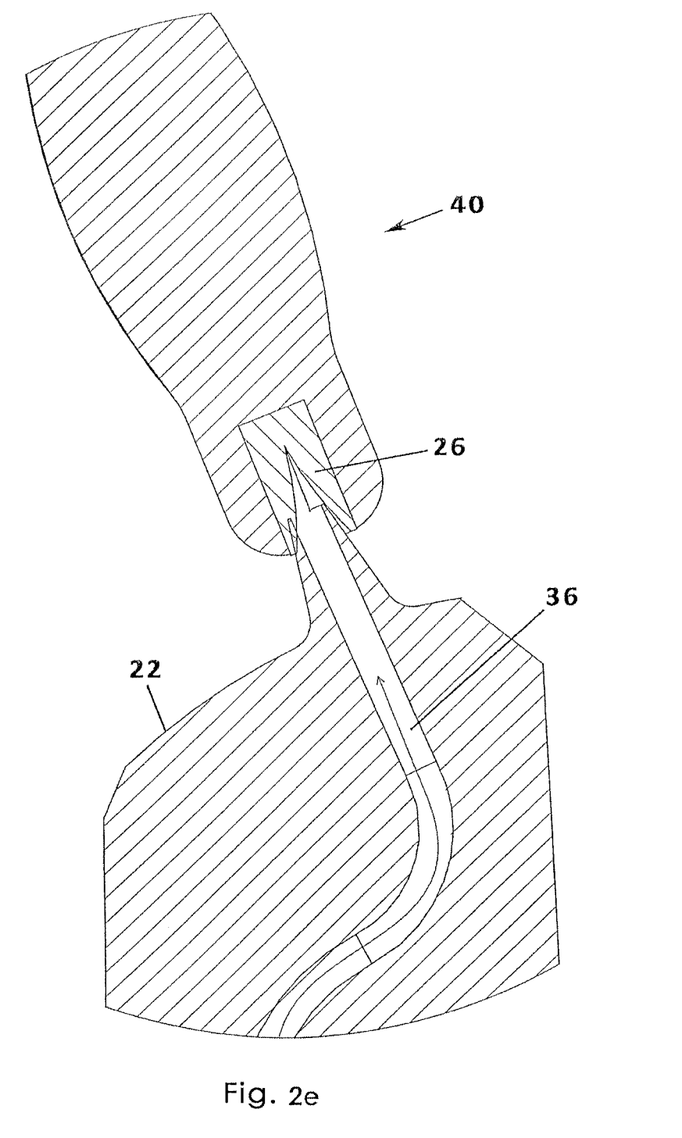
FIG. 2e is an isolated view on an enlarged scale taken from a portion of FIG. 2d.
Figure 3:
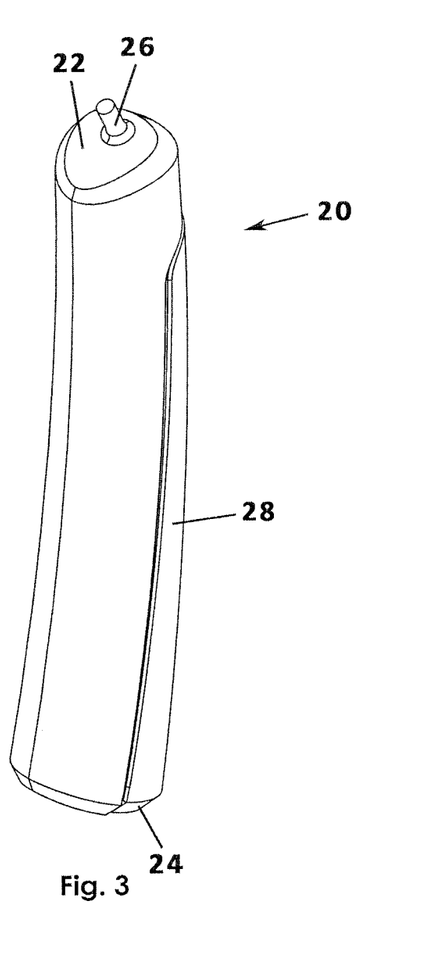
FIG. 3 is a side view of the eye ailment treatment apparatus as in FIG. 1 illustrated with the treatment head removed.
Figure 4:
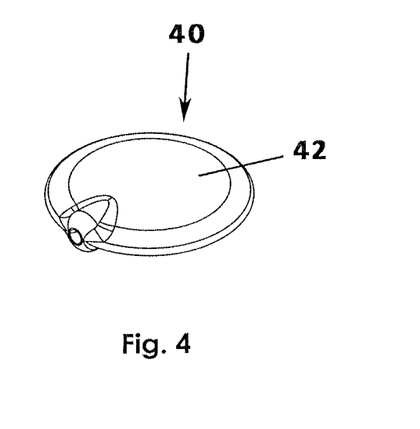
FIG. 4 is an isolated view of the treatment head removed from the handle.

An actuator 44, such as an actuator button, is situated on the outer wall of the case 20 and is operably connected to the water reservoir 30. The actuator 44 may be positioned on or embedded in the overmold 28 (FIG. 1). When the actuator button is pressed, a portion of the water reservoir 30 is compressed so that a predetermined quantity of water is injected from the water reservoir 30 to and through the outlet port 26 and into the treatment head 40. The outlet port 26 may be a one-way valve. In other words, water cannot exit through the outlet port 26 once received or injected therethrough. It is understood that a channel, such as with tubing 36 or a molded channel, may be included through which water is moved from the water reservoir 30 to the outlet port 26 (FIG. 2d). Preferably, operation of the actuator causing the water reservoir 30 to inject water is mechanical so that no battery is required although a battery operated pumping assembly is contemplated and would also work. More particularly, a spring pump 45 is coupled to the actuator 44 and operable to be compressed (FIG. 2d) when the actuator 44 is pressed downwardly and then automatically returns the actuator to its normal configuration (FIG. 2b) when pressure is removed from the actuator 46 such that pressing the actuator button causes a proportionate amount of water to be forced from the water reservoir 30 through the outlet port 26 and then resets. The spring pump 45, therefore, may be a compression spring. It will be appreciated, however, that references to the actuator being a spring pump may be considered references to equivalent structures such as other types of pumps, i.e. a slider-type pump, a squeeze/press, or the like. In other words, means for actuating the water reservoir 30 to force water out may be slightly different in configuration than described herein but are still I the spirit of the present disclosure.

In another aspect, the treatment head 40 may include an external portion 42 and an internal chamber. The external portion 42 includes an external surface constructed of a soft material, such as cotton, that is gentle when pressed against the skin of a user and especially against an eye of the user. Preferably, the external portion 42 has a planar configuration and may have a generally circular shape configuration. The internal chamber may include a bag or molded plastic reservoir that is unvented and from which water, once received, is not released. In other words, the internal chamber is impermeable and sealed against the release of water which is received via the outlet port 26 which includes a one-way valve 26. The internal chamber includes a material capable of generating an exothermic chemical reaction when it comes in contact with water. In an embodiment, the internal portion of the treatment head includes calcium chloride granules, calcium chloride being the material that generates an exothermic reaction when contacted by water from the water reservoir 30 when pumped into the internal chamber of the treatment head 40. To be clear, the exothermic reaction generates heat for heating the external portion 42 and which enables the treatment head 40 to impart heat to a user's eye region when touched thereto while the exothermic material and heated water remain inside the unvented internal chamber.

In an embodiment that is substantially similar to the embodiment disclosing use of calcium chloride, the internal portion may include a super absorbent polymer ("SAP") that is operable to absorb the water that is pumped into the internal portion of the treatment head 40. A super absorbent polymer is made from the polymerization of acrylic acid blended with sodium hydroxide in the presence of an initiator to form a poly-acrylic acid sodium salt (sometimes referred to as sodium polyacrylate). Superabsorbent polymers are commonly made from the polymerization of acrylic acid blended with sodium hydroxide in the presence of an initiator to form a poly-acrylic acid sodium salt (sometimes referred to as sodium polyacrylate).

In addition, the exothermic material may include or be mixed with a plurality of fibers and inert materials that are known to retain the heat that is generated by the exothermic reaction described above. For instance, fibers marketed under the trade name Outlast® Technologies include phase change materials (PCM) that absorb, store and release heat and may be encapsulated in a polymeric shell.

Figure 5A:
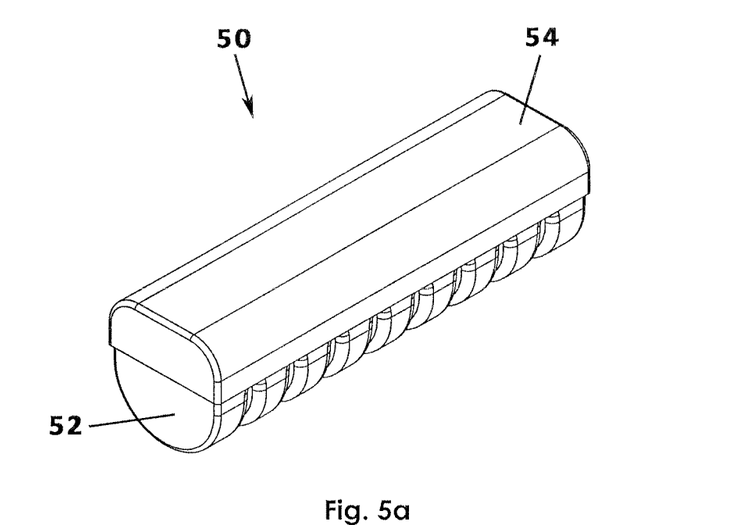
FIG. 5a is a perspective view of a replacement treatment head housing according to the present invention.
Figure 5B:
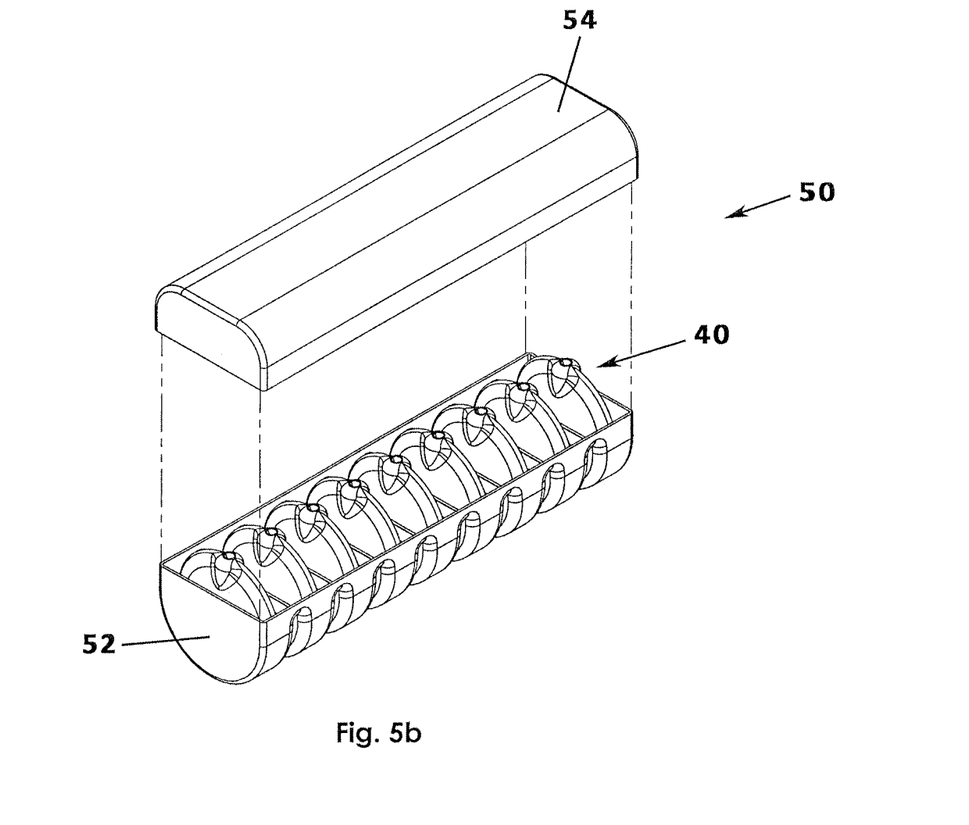
Figure 6A:
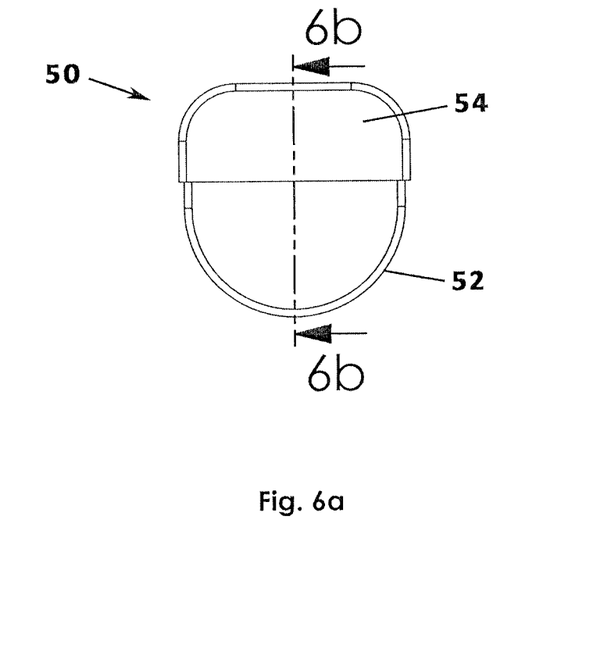
Figure 6B:
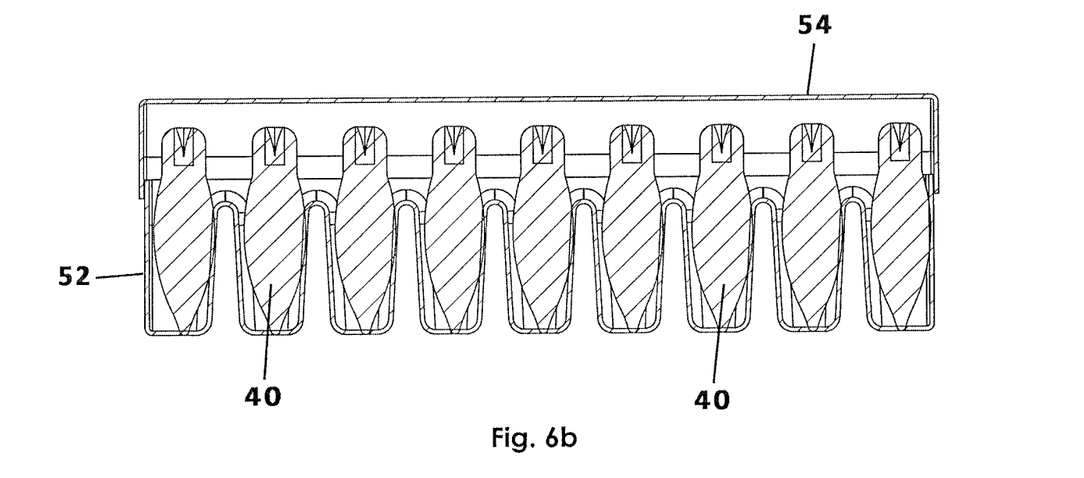
Figure 7:
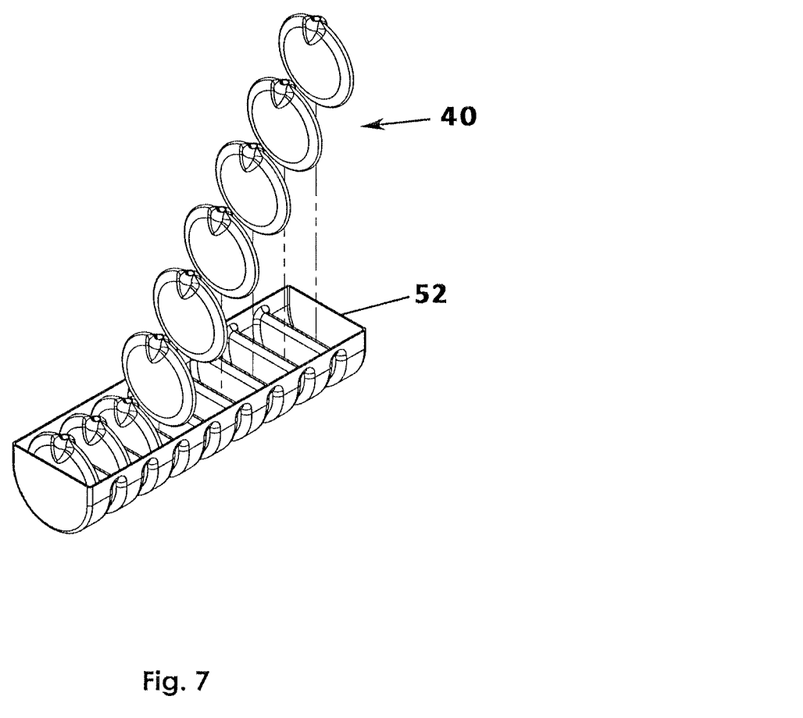
FIG. 7 is an exploded view of a bottom tray of the replacement treatment head housing.

In another aspect, the treatment head 40 of the eye ailment treatment apparatus 10 may be removable from the outlet port 26 and interchangeable with a replacement treatment head having the same structure and function as the treatment head 40 first described above. In some embodiments, a treatment head 40 may be for a single treatment session and then discarded. A replacement treatment head may then be coupled to the outlet port 26 for a next use. Preferably, the eye ailment treatment apparatus 10 includes a plurality of replacement treatment heads initially stored in a storage housing 50. The storage housing 50 may include a bottom tray 52 uniquely configured to receive the plurality of replacement treatment heads (for example a quantity of 10 treatment heads) in a longitudinally adjacent arrangement (FIG. 5b). More particularly, the bottom tray 52 may include an elongate and generally U-shaped configuration and may be arranged with a plurality of compartments, each compartment having a shape configuration that is complementary to a shape configuration of a treatment head whereby to receive it snugly in a respective compartment. The storage housing 50 may include a lid 54 that is configured to fit snugly to the bottom tray 52 yet is selectively removable to gain access to the plurality of replacement treatment heads therein. In other words, the lid 54 is movable between a deployed configuration coupled to the bottom tray 52 that prevents access to the contents of the bottom tray 52 and a removed configuration displaced from the bottom tray 52 that allows access to the contents of the bottom tray 52.

Figure 8:
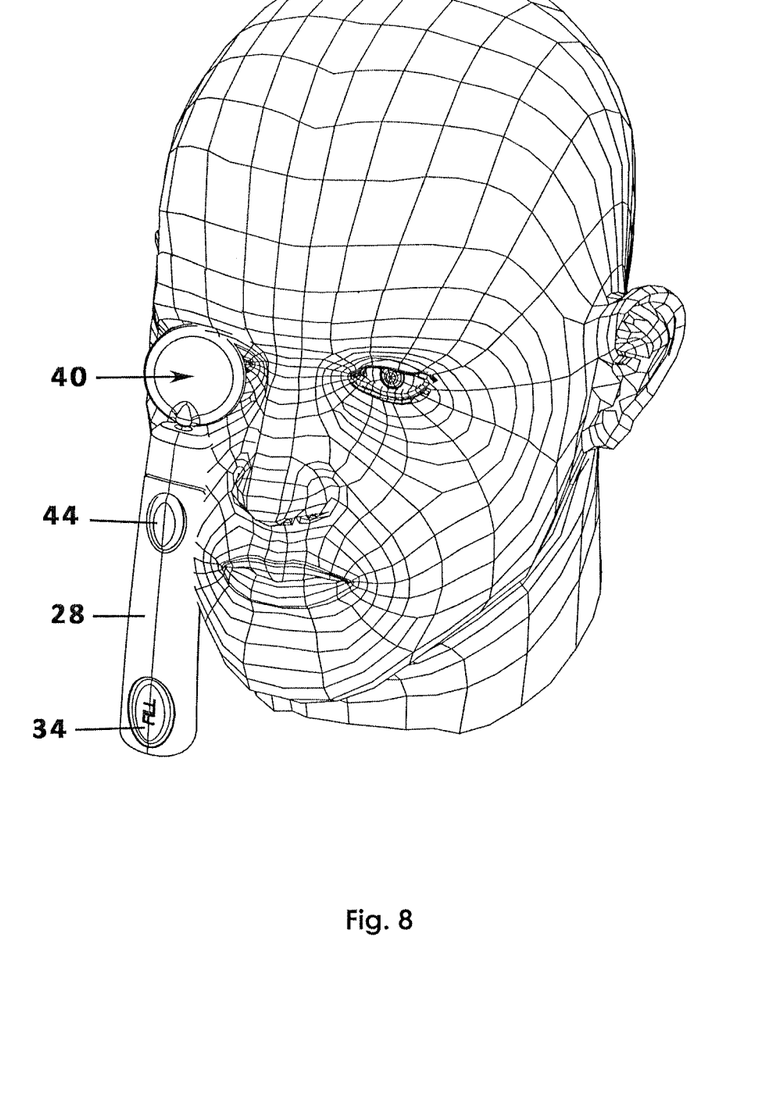
FIG. 8 is a perspective view of the eye ailment treatment apparatus in use on a patient.

FIG. 8 illustrates the eye ailment treatment apparatus 10 in use by a patient. Specifically, the user would press the actuator 44 to eject a predetermined quantity of water from the water reservoir 30 into the interior chamber of the treatment head 40 via the outlet port 26 and related tubing 36 or molded channels. Infusion of water into the internal chamber results in an exothermic reaction and causes heat to be generated and conducted to the external portion or pad of the treatment head 40. The heated pad may then be pressed gently against the stye on or in the eye of the patient whereby to treat the stye. This may be done with or without additional medicaments placed on the external portion (i.e. pad) of the treatment head. Following use, the treatment head 40 may be removed, discarded, and replaced with a replacement treatment head as described above.

It is understood that while certain forms of this invention have been illustrated and described, it is not limited thereto except insofar as such limitations are included in the following claims and allowable functional equivalents thereof.

The invention claimed is:

1. An eye ailment treatment apparatus, comprising:
   a case having an outer wall that has a front end and a rear end opposite said front end, said outer wall defining an interior area and having an outlet port at said front end;
   a water reservoir positioned in said interior area and in operable communication with said outlet port;
   an actuator on said outer wall in communication with said water reservoir and operable for pumping water out of said water reservoir and into said outlet port when actuated;
   a treatment head removably coupled to and in fluid communication with said outlet port, said treatment head comprising:
      an external portion having a planar and circular shape configuration complementary to a shape of a human eye and constructed of a soft material operable to make contact with a user's eye; and
      an internal chamber constructed of a molded plastic reservoir that includes an exothermic material that generates heated water when mixed with water, wherein said internal chamber is unvented and sealed against a release of said generated heated water; and
   a plurality of replacement treatment heads, each replacement treatment head being removably coupled to said outlet port when said treatment head coupled to said outlet port is removed, each said replacement treatment head including an external surface having a planar and circular shape configuration and constructed of a soft material for contact with a user's eye and including an unvented internal chamber that includes an exothermic material that generates heat when mixed with water.

2. The eye ailment treatment apparatus as in claim 1, wherein said exothermic material in said internal chamber of said treatment head includes granular calcium chloride that causes an exothermic reaction that generates heat when the water from said water reservoir is injected into said internal chamber through said outlet port.

3. The eye ailment treatment apparatus as in claim 1, wherein said exothermic material is a super-absorbent polymer ("SAP") operable to absorb the water when pumped into the internal chamber through said outlet port and to form a gel thereby in said internal chamber of said treatment head.

4. The eye ailment treatment apparatus as in claim 1, wherein said outer wall is a continuous side wall having an elastomeric overmold positioned on a portion of a top surface of said continuous side wall, said actuator being a button embedded in said overmold.

5. The eye ailment treatment apparatus as in claim 2, wherein said case includes a fill port in fluid communication with said water reservoir, said fill port including a one-way valve movable between an open configuration allowing access to said water reservoir and a closed configuration not allowing access to said water reservoir.

6. The eye ailment treatment apparatus as in claim 1, further comprising a storage housing having a bottom tray configured to receive said plurality of replacement treatment heads, each said replacement treatment head having an external surface constructed of a soft material for contact with a user's eye and having an internal chamber that includes a exothermal material that generates heat when mixed with water.

7. The eye ailment treatment apparatus as in claim 6, wherein:
   said bottom tray has an elongate and U-shaped configuration having a plurality of compartments for receiving said plurality of replacement treatment heads, respectively;
   said storage housing further comprising a lid removably coupled to said bottom tray and movable between a deployed configuration blocking access to said plurality of replacement treatment heads and a removed configuration allowing access to said plurality of replacement treatment heads.

8. The eye ailment treatment apparatus as in claim 1, further comprising a spring pump operably coupled to said actuator and movable between a compressed configuration when said actuator is pressed and an expanded configuration automatically returning said actuator to a normal configuration after said actuator has been actuated to inject water from said water reservoir into said internal chamber of said treatment head via said outlet port.

\* \* \* \* \*